United States Patent [19]
Cosmetto et al.

[11] Patent Number: 5,127,412
[45] Date of Patent: Jul. 7, 1992

[54] SKIN TENSIONING

[76] Inventors: Aristodeme J. Cosmetto, 6745 S.W. 27th Ave., Miami, Fla. 33155; Bernard H. Cohen, 9150 S.W. 87th Ave., Miami, Fla. 33176

[21] Appl. No.: 680,250

[22] Filed: Apr. 3, 1991

Related U.S. Application Data

[63] Continuation of Ser. No. 493,413, Mar. 14, 1990, abandoned.

[51] Int. Cl.$^5$ ............................................... A61B 17/04
[52] U.S. Cl. .................................. 128/898; 606/218; 606/232
[58] Field of Search ................. 606/74, 148, 216, 215, 606/218, 217, 232, 233, 103, 105; 128/898

[56] References Cited

U.S. PATENT DOCUMENTS

| | | | |
|---|---|---|---|
| 345,541 | 7/1886 | Reichardt | 606/216 |
| 3,650,274 | 3/1972 | Edwards et al. | 606/233 |
| 3,971,384 | 7/1976 | Hasson | 606/218 |
| 4,210,148 | 7/1980 | Stivala | 606/232 |
| 4,535,772 | 8/1985 | Sheehan | 606/218 |

FOREIGN PATENT DOCUMENTS

| | | | |
|---|---|---|---|
| 1064940 | 1/1984 | U.S.S.R. | 606/148 |
| 2114894 | 9/1983 | United Kingdom | 606/148 |

OTHER PUBLICATIONS

Expansion of an Area of Skin by Progressive Distension of a Subcutaneous Balloon—Charles D. Newmann, M.D.—Feb., 1957.
Development of Adjacent Flaps Using a Temporary Expander—Chademir Radovan, M.D.
Tissue Expansion—Gordon H. Sasaki, M.D.—1987 Dow Corning.
The Physical Properties of Skin—Thomas Gibson, Chapter 2 General Principles.
Soft Tissue Expansion: Concepts and Complications—Manders, M.D., et al—Plastic and Reconstructive Surgery—Oct., 1984.
Reconstruction of the Tip of the Nose . . . —Hirshowitz, et al—Reconstruction of the Tip of the Nose, vol. 77, No. 2—Plastic & Reconstructive Surgery—Feb., 1986.
Presuturing—A New Technique for Closing Large Skin Defects—Liang M.D., et al, vol. 81, No. 5—Plastic and Reconstructive Surgery, May 1988.
Wound Closure by Skin Traction—A. H. Bashir, British Journal of Plastic Surgery 1987, 40, 582–587, Ideal Laparatomy Closure, Laparatomy Closure, The American Surgeon, pp. 582–584, Aug. 1976.

*Primary Examiner*—Michael H. Thaler
*Attorney, Agent, or Firm*—Jack E. Dominik

[57] ABSTRACT

The skin tension set includes an anchor member having a body portion and a plurality of suture guides along its sidewalls and bottom coupled by a single suture loop to the anchor is a winder. The winder has a body portion with suture guides at the bottom not unlike the anchor portion. In addition, however, the winder includes a central reel with suture anchoring guides, a ratchet at one end, and a drive preferably with the form of a detachable knurled knob at the other. According to the method of the present invention, the wound is sutured with preferably a monofilament suture by passing the suture through one suture guide in the winder reel and then through and out the bottom of the winder bottom across the wound, through the skin on the opposite side of the wound, looped through the anchor and similarly back to the winder and knotted. Thereafter, in accordance with the method of the present invention, the winder is ratcheted by the surgeon to apply tension through the single loop of suture material in parallel fashion across the wound, thus stretching the skin and/or closing the wound. When tensioning is performed before the actual surgery, it would be for the purpose of stretching the skin in anticipation of subsequent surgery.

2 Claims, 10 Drawing Sheets

SKIN TENSIONING

CROSS-REFERENCE TO RELATED APPLICATIONS

The present application is a continuation of application Ser. No. 493,413 filed Mar. 14, 1990 now abandoned, by the same inventors herein and entitled "Skin Tension Set and Method".

FIELD OF THE INVENTION

The present invention relates to the subject matter of stretching or expanding skin for the purpose of facilitating the difficult closure of large skin wounds that might be encountered in the field of general and reconstructive plastic surgery. The invention deals with a method and apparatus which may be used for three purposes: (1) to generate additional tissue for the sutured closure of surgically created skin defects in either their preoperative or intraoperative state; (2) to traction-assist the natural contraction and non-sutured closure of open skin defects which may have been surgically operated or may have been the result of trauma or pressure (decubiti); and (3) to act as an adjustable retention suture bolster in the post-operative phase of general surgical procedures (i.e. abdominal surgery).

SUMMARY OF THE PRIOR ART

Traditionally when surgeons are faced with medium sized defects, the margins of which are not easily approximated, they will undercut the wound edges a few centimeters in order to mobilize tissue for a relaxed closure. If faced with large defects that would be even more difficult to close, they may perform a wound covering skin graft by bringing in a completely detached portion of extra tissue from a distant site on the body. They may also construct a wound cover called a skin flap by elevating reduncant, contiguous, near-by tissue and then partially detaching it, moving it, and seating it into the defect. The notion of actually stretching or expanding adjacent skin to generate extra tissue for wound cover was not described until the 1970's. Historically, Gibson was one of the first to observe that skin, when intermittently tensioned, will significantly elongate beyond its intrinsic limits, without damage to its physical integrity. This phenomenon called "mechanical creep" is attributed to the collagen fibers' ability to uncoil, align, and compact more closely together in response to a sustained, applied load. Collagen fibers have no power of retraction. When stretched skin is anchored to a fixed point, the natural elasticity imparted by the relatively weak elastic fibers, is unable to revert the skin back to its original state. Three clinically successful skin stretching methods have been described in the surgical literature (Hirshovitz, Liang, and Bashir) and have been offered as alternatives to skin grafts and skin flaps. These three methods utilize no special apparatus other than conventional suture material and skin hooks.

Hirshovitz reported that he could effectively stretch skin in its intra-operative state by grasping the free edge with skin hooks and tugging on it in a cyclic fashion. He found that the stretched skin would significantly elongate over a period of minutes. He used only conventional skin hooks and did not quantify his manually applied load. It is the generally held impression that cyclic loading is less traumatic to issue than is continuous loading, because compressed blood vessels are allowed to decompress.

Liang reported that he could effectively stretch skin in its intact, preoperative state by folding the proposed surgical margins of the intact skin toward one another and suturing them together. After continuously holding the skin in tightly fixed apposition for a period of hours, the ligature was removed. When excision was subsequently performed, the "presutured" wound edges could be approximated with 40% less tension. Liang used only conventional suture material, and did not quantify the load in the ligature. Overloading the tension on the skin would have resulted in traumatic tearing at the suture material's entry site. Underloading would have resulted in inefficient stretching.

Bashir reported that he could effect the natural and gradual contraction of open skin defects (healing by secondary intention). He found that when the free edges of a non-surgically created traumatic defect are slowly and gently pulled into apposition by traction, over a period of weeks, the granulating would will close more rapidly than it would be expected to without the traction assist. He used only conventional suture ligature wires and threaded them in parallel to the wound edges. To these he attached a ligature wire cross member and applied continuous tension by manually twisting the cross member on itself, in a non-quantified fashion. The crude manner in which the wire was attached to the skin edges was undoubtedly traumatic.

In 1957, Neumann described for the first time an inflatable tissue expander—a rubber balloon implanted adjacent to the proposed excision site. This essentially introduced the notion of "tissue expansion" which did not become a popular technique in plastic and reconstructive surgery methodology until Radovan introduced the silastic silicone bladder in 1976. Silastic inflatable bladders are manufactured under various patents in many sizes, shapes, and valve configurations. When describing an apparatus to stretch skin, the surgical community universally associates the term "tissue expander" with an incrementally filled silastic implanted bladder which acts as a skin tensing apparatus. The device and method in all its details have been the subject of over one hundred scientific articles with a recent review by Manders.

If the tissue expander is used preoperatively, for example, in the case of tumor surgery, the device is implanted in a surgical pocket, adjacent to the tumor, and incrementally inflated. Weeks later, the device is removed during a second procedure in which the tumor is excised. The additional expanded tissue is used to close the large defect created by the tumor's absence. Two surgical procedures are obligatory.

If the tissue expander is used intraoperatively, for example, in tumor surgery, the tumor is excised, and a surgical pocket is created beneath both free edges of the large defect. A deflated tissue expander is placed into each lateral pocket, and the wound is temporarily sutured closed. The expanders are then inflated and deflated in a cyclic fashion until skin stretch occurs. The wound is reopened, and the devices removed, and the additional expanded tissue is used to close the defect created by the surgical removal of the tumor. Sasaki observed tissue expansion up to two cm. after intraoperatively load cycling the apparatus for twenty minutes.

The inflatable tissue expander is associated with many complications arising from the additional surgical trauma required for creation of its deep subcutaneous pocket. The device itself is easily punctured, may leak or otherwise mechanically fail, appears cosmetically deforming when inflated, and most importantly may destroy the overlying skin by pressure necrosis because there are no means of measuring the tension on the skin as safeguard against over inflation.

In summary, the prior art as referred to above may be found in Gibson T. "The Physical Properties of Skin. Reconstruction Plastic Surgery" (ed:Converse) Chapter 2, P. 70; Hirshowitz, B., et al. Reconstruction Of the Tip of the Nose by Load Cycling of the Nasal Skin and Harnessing of Extra Skin. Plast. Reconstr. Surg. 77:316, 1986; Liang, M., et al. Presuturing a New Technique for Closing Large Skin Defects:Clinical and Experimental Studies. Plast. Reconstr. Surg. 81:694, 1987; Bashir, A. H., Wound Closure by Skin Traction: An Application of Tissue Expansion. Brit. Jour. of Plast. Surg. 40:582, 1987; Neuman, C. G. The Expansion of an Area of Skin by the Progressive Distension of a Subcutaneous Balloon. Plast. Reconstr. Surg. 19:124, 1957; Radovan, C. Adjacent Flap Development Using an Expandable Silastic Implant. presented at the annual meeting of the Amer. Soc. of Plast. & Reconstr. Surgeons, Boston, Mass., 1976; Radovan, C. Development of Adjacent Flaps Using a Temporary Expandable Silastic Expander. Plast. Surg. Forum 2:62, 1979; Manders, E. K., et al. Soft Tissue Expansion:Concepts and Complications. Plast. Reconstr. Surg. 74:493, 1984; Sasaki, G. H. Instruction Booklet:Intra-operative Tissue Expansion-Guidelines and Case Analysis. Available through Dow Corning Wright, 5677 Airline Road, Arlington, Tenn. 38002 (phone 901-867-9971). What is needed is a tissue expansion system that combines the simple features of externally applied suture methods with the sophisticated features of an incremental, adjustable tensing apparatus. The system should offer the diversity of being applicable to all clinical situations: preoperatively, intraoperatively, post-operatively (as a retention device) and apply to surgically created as well as non-surgically created wounds. The system should be applicable to surgical defects with either undercut or non-undercut edges. The system's tensing apparatus should be externally attached to eliminate the complications arising from subcutaneous surgical implantation. The attached apparatus should be of non-traumatic, smooth, curved, bolster design and be configured in such a way as to protect the skin from being lacerated by the tightly drawn suture ligature which it guides. The apparatus itself should be of such configuration as to allow integration with a separate measuring device (i.e. torque wrench) which would display applied tension and therefore minimize the complications of overstretching, or inefficiently of understretching. The path of the suture ligature through the apparatus should be non-binding and relatively free of friction in order that the tension transmitted to the torque wrench be accurately represented. The apparatus should have a tension releasing feature to accommodate those surgeons who prefer to use stress-relaxation cycle technique. The system should allow for easy attachment and removal and be compatible with currently available suture material and accepted suturing techniques and patterns. The system should have the capability of allowing simultaneous attachment of multiple devices in order to accommodate long or irregularly shaped wounds. The system should be durable, sterilizable, reusable and relatively inconspicuous when attached to the skin.

The present invention clearly relates to the notion of tensioning skin edges (in an adjustable controlled manner) for the purpose of expanding them or bringing them into apposition thereby effecting a less difficult and/or more rapid wound closure. However, the present invention may serve equally as well to adjust skin tension in situations where the tension on the sutures is from outside the ligature loop, and is not created by the surgeon's actual tightening of the suture. Such a situation exists in abdominal surgery, when the post-operative distending abdomen may cause fixed retention sutures to tighten and cause undue pressure on the abdominal skin.

This situation has been addressed by two devices which are available from Ethicon Corporation (see U.S. Pat. No. 3,650,274). One device entitled, a "retention suture bridge" is a plastic, disposable, truss bridge which elevates the post-operative retention ligature away from the skin. The apparatus is adjustable an be capable of relaxing or tightening the ligature which it guides. The tension which the surgeon chooses, by rotating a capstan, is determined by the amount of tension exerted by underlying edema or abdominal distention.

The entire length of the unit's base contacts the skin and because it is non-compressible, it fixes the skin edges at a predetermined distance. The device is not only incapable of performing the function of stretching, expanding, or approximating skin edges, but the configuration of its base has a tendency to be non-bolstering. The other device entitled a "retention suture bolster" is a simple soft latex tube through which ligature is passed. It serves to prevent the retention ligature's cutting into the distended abdominal skin. Although its edges are curved lengthwise, its ends are angled and can cause an inflammatory response with reaction both at the site of the suture exit from the skin and along the entire length of the suture itself.

The present invention not only functions as a tissue expanding device but may additionally function as an adjustable bolstered retention suture device. In fact, it combines the advantageous properties of both presently available retention suture devices, while eliminating their disadvantages. The present invention directs the retention suture ligature beneath the skin, rather than along a plastic truss or through a latex tube which rests directly on the freshly cut edges of the wound. The present invention applies bolstered pressure to areas lateral to the wound, and the units may be spaced as widely as the surgeon chooses, while never resting on the cut and sutured length of the incision. Should the abdomen become distended, the apparatus can be momentarily disengaged and then ratcheted to a looser setting, thereby relieving the detrimental effect which external tension has placed on the retention ligature loop. The unit need not be removed, or the knot untied.

SUMMARY OF THE INVENTION

The present invention is directed to a surgical apparatus which is, in effect, a tension set and a method of skin expansion. The tension set includes an anchor member having a body portion and a plurality of suture guides along its sidewalls and bottom coupled by sutures to the anchor is a winder. The winder has a body portion with suture guides at the bottom not unlike the anchor portion. In addition, however, the winder includes a central reel with suture anchoring guides, a ratchet at one end, and a drive means preferably with the form of a detachable knurled knob at the other. According to the method of the present invention, the wound is sutured with preferably a monofilament suture by passing the suture through one suture guide in the winder reel and then through and out the bottom of the winder body. The suture then enters the full thickness of the skin, exits through the subcutaneous tissue and extends across the wound. It enters the subcutaneous tissue of the opposite side and is passed up and through the full thickness of the skin and then across the surface of the skin parallel to the length of the wound. It re-enters the skin and passes full thickness exiting through the subcutaneous tissue of the same side and then extends back across to the opposite side of the wound where it re-enters the subcutaneous tissue and passes up through the skin into the bottom of the winder body and then through a suture guide of the winder reel. It is then tied to the free end of the suture at the starting point. The externalized suture on the side of the wound opposite the winder and reel is grasped by the comb-like sidewall of the anchor member. Thereafter, in accordance with the method of the present invention, the winder is ratcheted by the surgeon to apply tension through the sutures in parallel fashion across the wound, and thus stretch the skin. This tensioning may take place before or during the operation while the skin extends under the gentle tension applied by the tension set. Depending on the surgeon's choice, the time may be minutes, hours, days or may be continuously cycled.

In view of the foregoing it is a principal object of the present invention to provide a tension set and method of using the same which is simple in construction, and uniform in its applicability, to the end that the skin may be tensioned and stretched over a wound for a sufficient period of time to stretch it to the point where it can be sutured together under minimal tension cut and the closure of the wound applied in such a fashion that proud flesh, and other extraneous scarring is avoided.

Another object of the present invention is to provide a tension set and method for using the same by which the skin can be stretched for a period of time prior to the operation and the patient will be ambulatory during such time period, and yet safety and assuredness of the skin stretch is provided.

A further object of the present invention is to provide a tension set and method which can be applied by more than one tension set where the wound is extremely long. A related object of the invention is to provide such a tension set and method whereby the tension in parallel sutures can be varied in order to apply the same equally or disproportionately depending upon the position of the wound.

Yet another object of the present invention is to provide a tension set and method which can be applied to the edges of a skin defect which is contracting by secondary intention—such as a traumatic ulcer. This would be a defect in which no sutured closure is planned. The tension set and method provides a facilitating effect of accelerating the natural contraction and closure of the wound by gentle sustained tension over a sufficient period of time.

A further object of the present invention is to provide a tension set and method of post-operative retention suturing which is capable of being adjusted to tension fluctuations caused by edema and abdominal distention.

A still further object of the present invention is to provide a tension set and method which allows quick release of the applied tension without necessary removal of the apparatus from the skin.

Another object of the present invention is to provide a tension set and method which is minimally traumatic to the skin by designing it with curved smooth edges and enclosed passages through which tightly drawn suture material is guided.

BRIEF DESCRIPTION OF THE DRAWINGS

Further objects and advantages of the present invention will become apparent as the following description to an illustrative embodiment and method proceeds, taken in conjunction with the accompanying drawings, in which:

FIG. 1 is a proposed surgical margins sketching drawn on the skin prior to an operation;

FIG. 2 shows the skin tensioning set sutured to the skin, before surgery, in such a manner as to fold the tumor upwardly;

FIG. 3 is a subsequent showing to FIG. 2 with the tension set tightened and lateral areas of the skin are stretched;

FIG. 4 is an end view of that shown in perspective in FIG. 3;

FIG. 5 shows the skin tensioning sets sutured to the skin, before surgery, in such a manner as to fold the tumor beneath the set;

FIG. 6 shows the skin tensioning set tightened with the stretching of lateral areas;

FIG. 7 shows the skin tensioning set removed and the tumor excised along the proposed margins;

FIG. 8 discloses the full thickness of the defect which results from excision of the tumor;

FIG. 9 shows the tension set attached to the margins of an open defect at the time of surgery and illustrating the hand of the surgeon and needle and suture as applied;

FIG. 10 shows the tension set fully attached with the suture knot tied;

FIG. 11 shows the reel being cranked while held by a wrench member to stabilize;

FIG. 12 illustrates lateral skin stretches as margins approach one another;

FIG. 13 discloses the tension being released by raising the gears off the tooth. This is useful in cycling;

FIG. 14 discloses what happens as the skin elongates and the slack is picked up by further cranking. The margins eventually meet one another. This Figure also illustrates how the tension set may be applied to an abdominal wound and function as an adjustable post-operative retention device;

FIG. 15 shows the wound after the tension set has been removed with the relaxed edges as traditionally sutured;

FIG. 16 is an alternative to that shown in FIG. 14 where the active member such as the winder can be substituted for the non-active member such as the anchor, and one or the other or pairs serve as a non-adjustable post-operative retention device after the wound has been traditionally sutured;

DESCRIPTION OF PREFERRED EMBODIMENTS

The skin tension set is a new surgical device/instrument which can be easily attached to the skin in order to facilitate the difficult closure of large skin wounds. Utilizing the established biomechanical and visco-elastic principles of relaxation and mechanical creep, the device is able to mobilize otherwise unavailable skin for difficult surgical closures. In addition, the device may also be used as a retention suture. The device may also be applied to non-difficult surgical closures in order to reduce the necessity for wound edge undercutting. Because multiple devices may be simultaneously attached, the length of the closure is not a limiting factor. When used in conjunction with an optional torque wrench, the applied skin tension can be directly controlled and monitored in order to prevent inadvertent tissue damage by over-stretching. The unique design of the skin tension set renders it extremely durable, reusable, mechanically simple, low in profile, and minimally traumatic to the skin. The device also has a quick release feature which allows its operator the option of stretch-relaxation cycling. Although it is most effective as a preoperative and intraoperative tissue expander, it may also serve post-operatively as a retention suture bolster which is capable of adjusting to tension fluctuations caused by edema or abdominal distention. It may also serve as a traction device which facilitates the contraction of open granulating defects for which no sutured closure is planned. Typical clinical applications would include wide linear excisions, alopecia reduction surgery, tissue flap expansion, laparoptomy retention suturing, and traction-assisted closures of open defects due to trauma, Moh's surgery, and decubiti.

Figure 2:
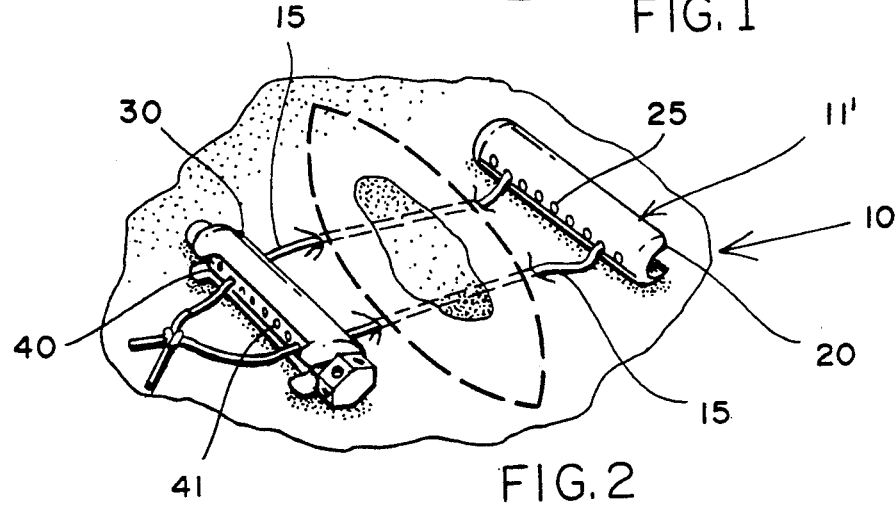

The details of the tension set 10 as shown particularly in FIG. 2 will be best understood in conjunction with a description of the method of the use of the skin tensioning device and the method of the patent. This breaks down into intraoperative usage, pre-operative usage, an alternative embodiment of pre-operative usage, and a usage for non-adjustable post-operative retention. These will be set forth below under separate subheadings.

INTRA-OPERATIVE USE OF APPARATUS

Figure 1:
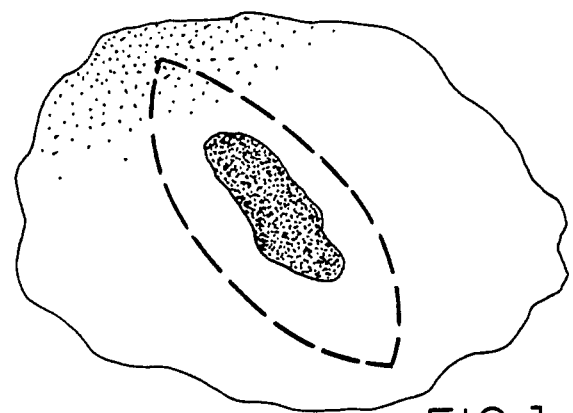
FIGS. 1-16 disclose various aspects of the tension set for intra-operative use of the set, preoperative use of the set, an alternative preoperative use of the set, and finally a use of the set or a portion of the apparatus for post-operative retention. Taken in this context.
Figure 7:
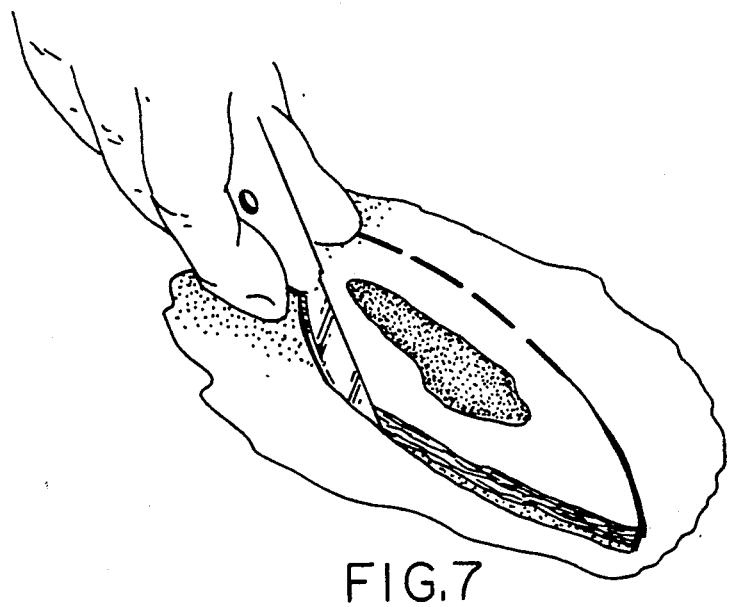
Figure 8:
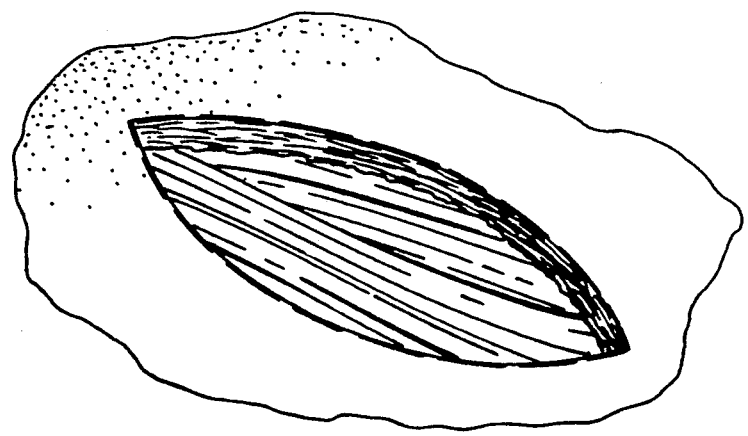
Figure 9:
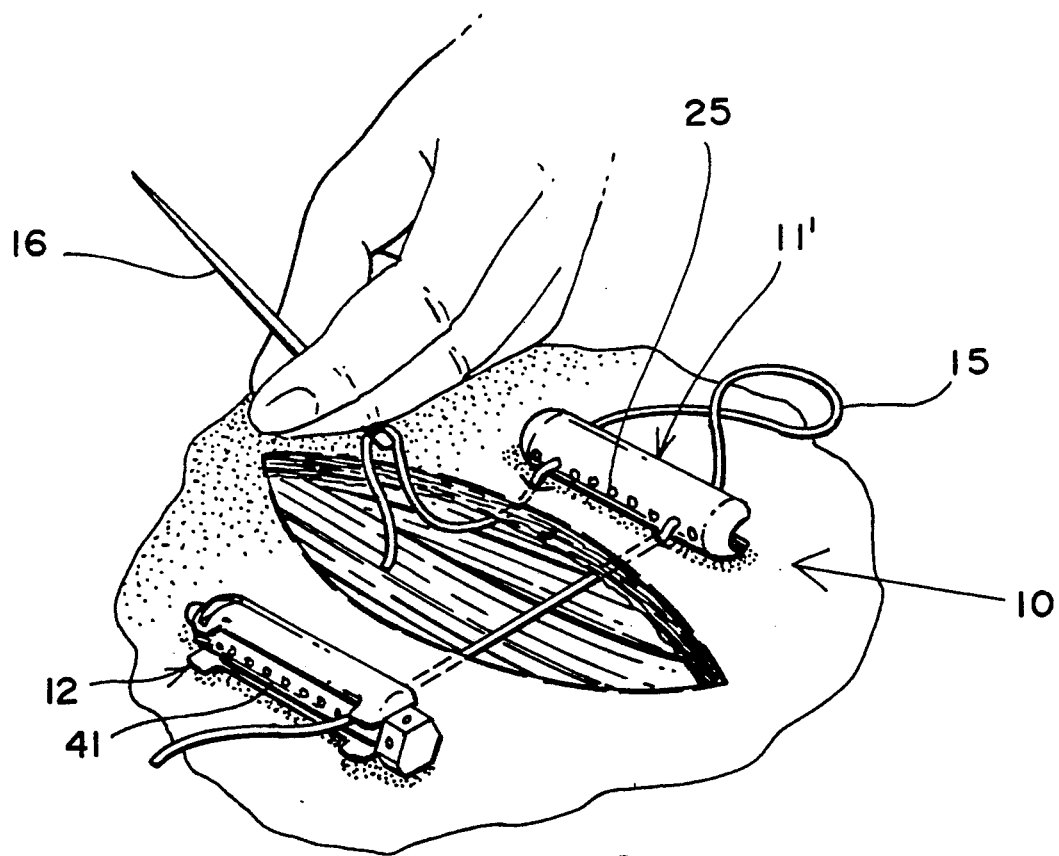
Figure 11:
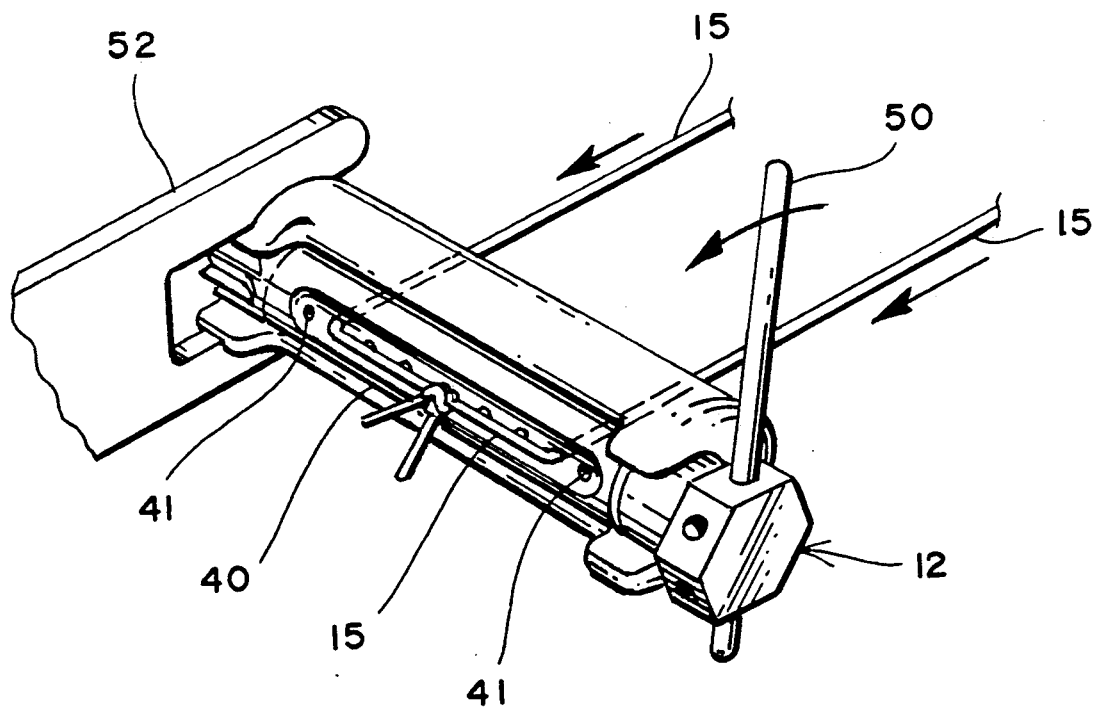
Figure 12:
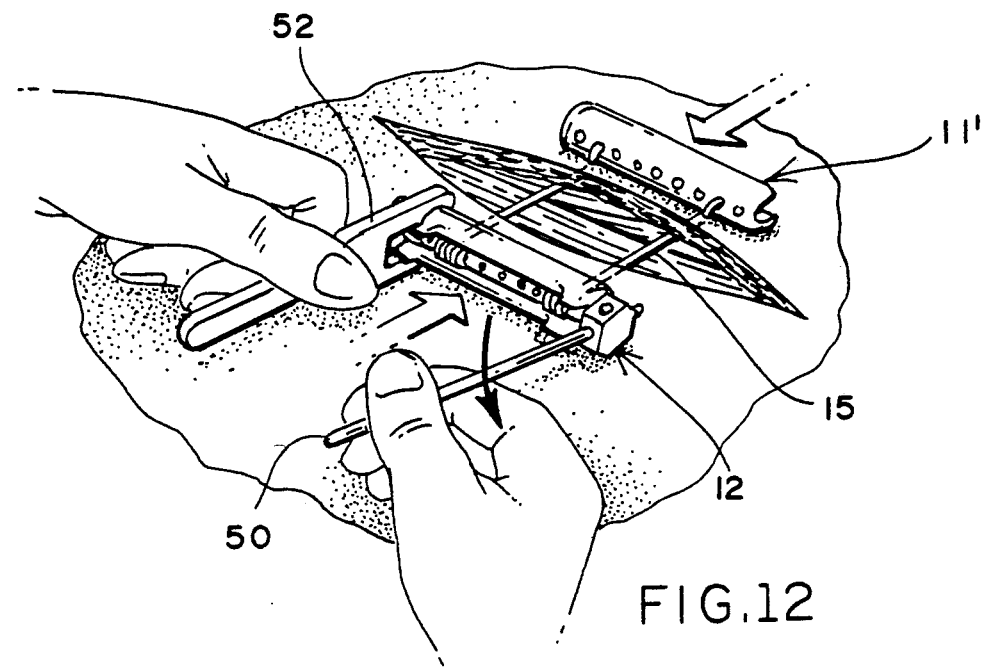
Figure 13:
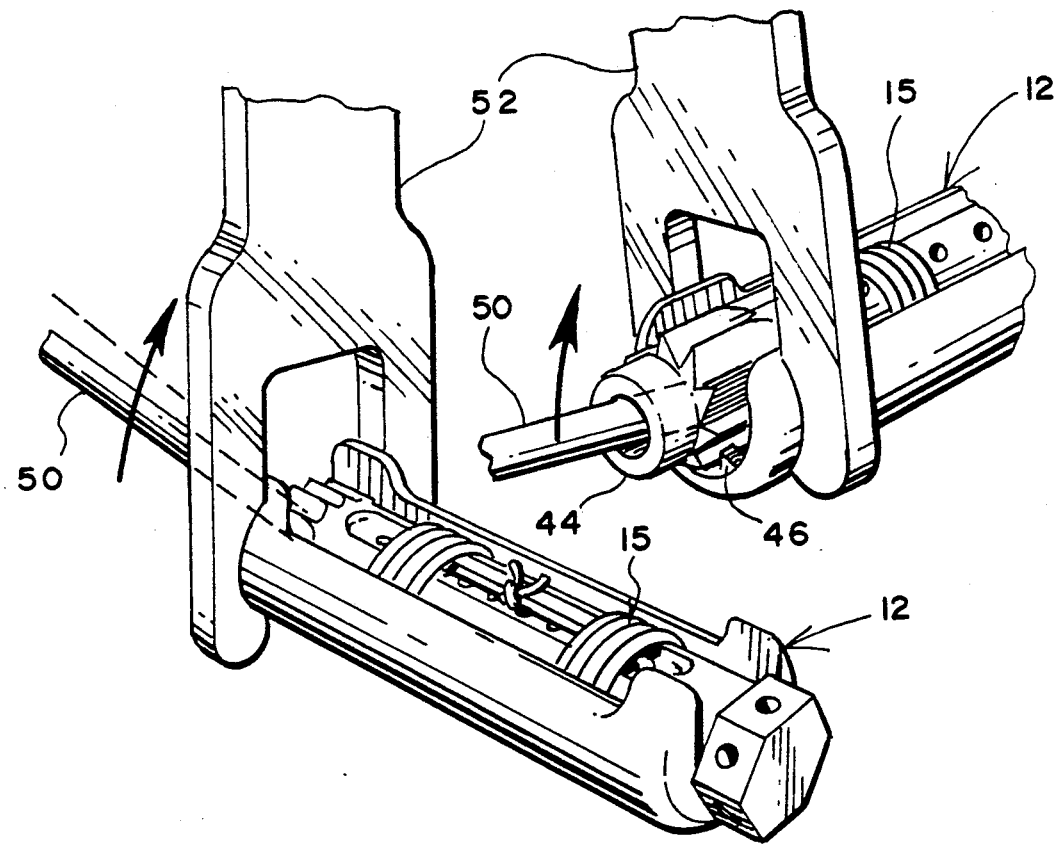
Figure 14:
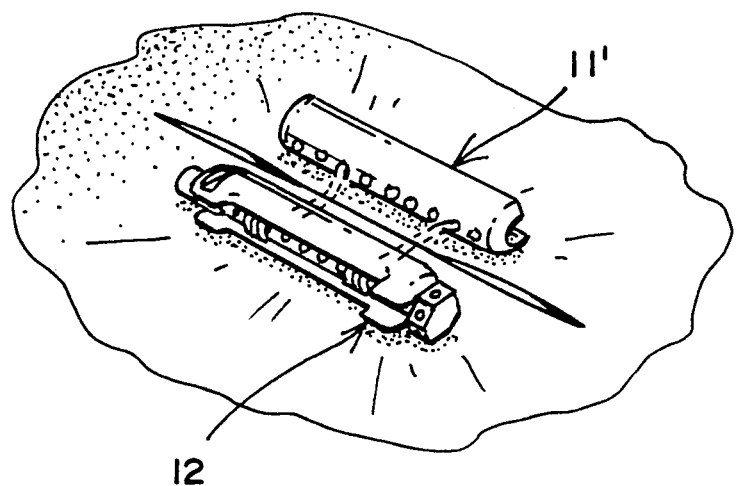
Figure 15:
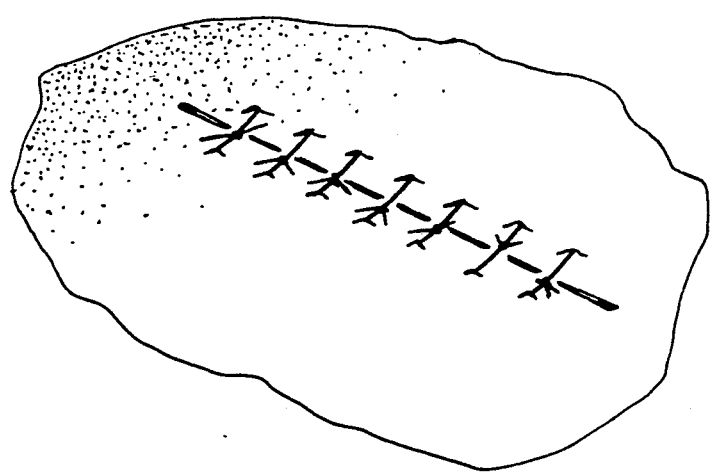

In the intra-operative use of the skin tensioning set 10, as noted in FIG. 1, the proposed surgical margins are drawing on the skin. Thereafter, as shown in FIG. 7, the tumor is excised along the proposed margins. Following this procedure, the wound appears as shown in FIG. 8 with the full thereafter, as shown in FIG. 9, the tension set is fully attached and a knot is thereafter tied where the suture 15 enters into the winder 12. Thereafter, as shown in FIG. 11, the winder 12 is cranked by means of the crank 50 while the winder 12 is held by means of the stabilizer 52. Sequentially thereafter, as shown in FIG. 12, the lateral skin stretches as the margins approach one another. Finally, as shown in FIG. 13, the tension is released by raising the ratchet gears off the tooth in a manner which is also useful in cycling. As shown in FIG. 14, as the skin elongates, slack may be picked up by further cranking and then the margins eventually meet each other. Finally, as shown in FIG. 15, the tension set 10 is removed and the defect with relaxed edges is traditionally sutured as shown. In special situations, such as the elongation of a very small or delicate skin flap, the non-active member may be omitted. The suture loop would be attached directly to the leading edge of the skin flap and then directed towards and passed through the active member which would be stationed at a more distant site.

Pre-Operative Use of Skin Tensioning Set

Figure 3:
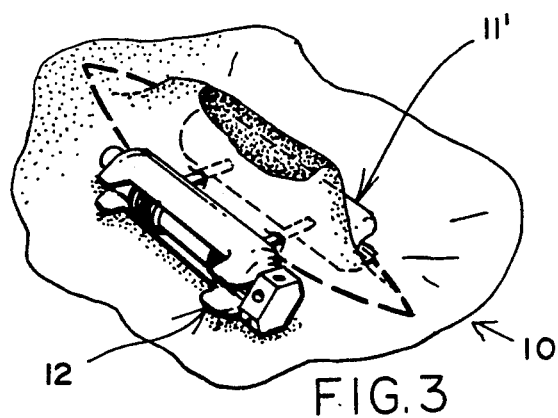
Figure 4:
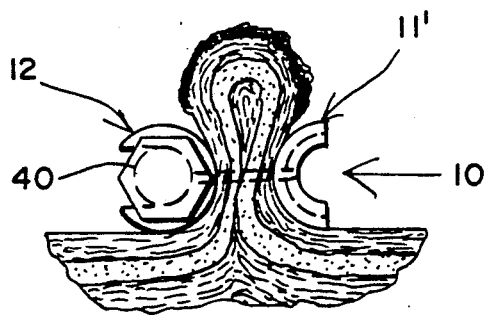

The pre-operative use of the tension set begins with drawing the proposed margins on the skin as shown in FIG. 1. The same proceeds as shown in FIG. 2 with the tension set including the anchor portion 11 and the winder portion 12 sutured to the skin, before surgery, in a fashion to fold the tumor upwardly. Thereafter, as shown in FIG. 3, the skin tensioning set 10 is tightened and the lateral edges are stretched. Finally, as shown in FIG. 4, the end view of FIG. 3, the skin is all raised and the tumor is folded upwardly for removal. Then, as shown in FIG. 7, the apparatus is removed and the tumor excised along proposed margins. FIG. 8 describes thereafter the full thickness defect which results from the removal of the tumor with the edges being prestretched. Thereafter, as shown in FIG. 15, the relaxed defect is traditionally sutured.

Alternative Pre-Operative Use of Apparatus

Figure 5:
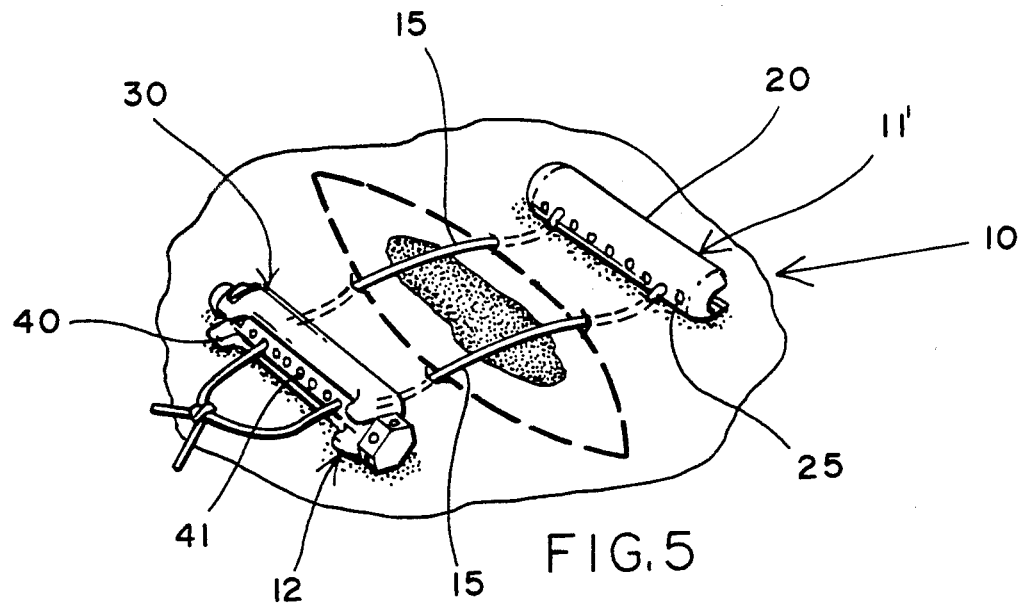
Figure 6:
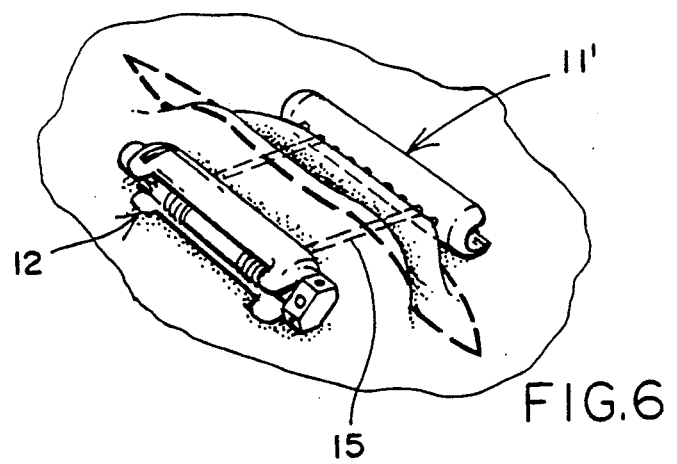

Here again the proposed surgical margins are drawn on the skin as shown in FIG. 1. Thereafter, the tension set is sutured to the skin as shown in FIG. 5 prior to surgery, but in such a manner as to fold the tumor beneath the skin tension set. Subsequently, as shown in FIG. 6, the apparatus is tightened and lateral areas are stretched. Thereafter, upon conclusion of the stretching, the conclusion of the preoperative use of the apparatus proceeds as described with regard to FIGS. 7, 8, and 15 above.

Alternative Post-Operative Retention

Figure 16:
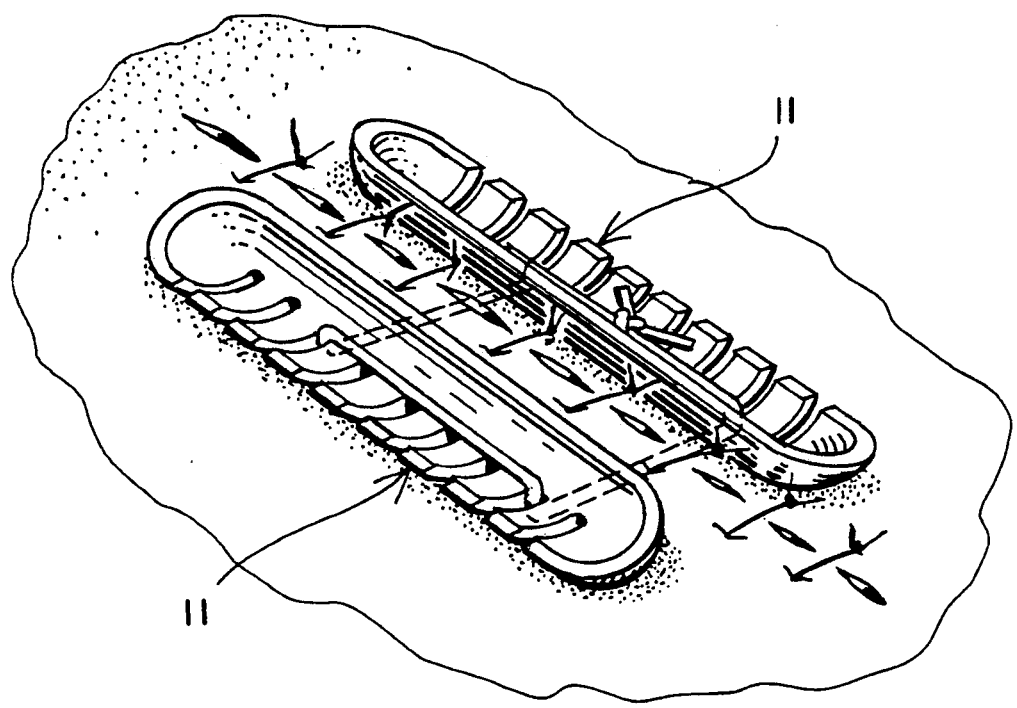

In FIG. 16 an alternative to the post-operative tension as shown in FIG. 14 is set forth where it will be seen that two opposed anchor members remain tied together on opposite sides of the wound with the suture in place over both. The suture is knotted optionally at either one of the anchor members 11 or the other anchor member 11.

Summary of Method

Intra-Operative Use of Apparatus

Figure 10:
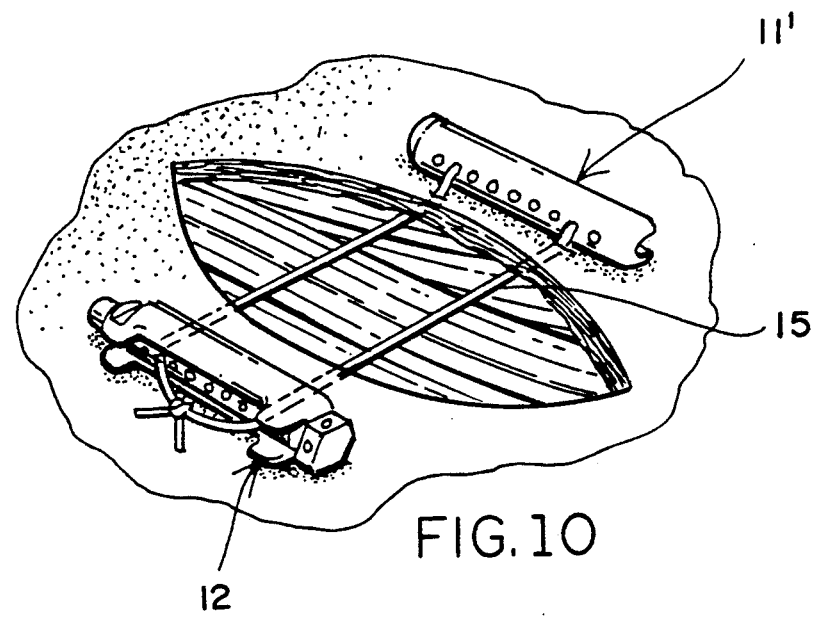

FIG. 1: Proposed surgical margins drawn on skin.
FIG. 7: Tumor excised along proposed margins.
FIG. 8: Full thickness defect resulting from excision of tumor.
FIG. 9: Apparatus attached to margins of open defect at time of surgery.
FIG. 10: Apparatus fully attached and knit tied.
FIG. 11: Active member is cranked while held by wrench to stabilize.
FIG. 12: Lateral skin stretches as margins approach one another.
FIG. 13: Tension released by raising gears off tooth. Useful in cycling method.
FIG. 14: As skin elongates, slack is picked up by further cranking. Margins eventually meet one another.
FIG. 15: Apparatus removed and defect with relaxed edges is traditionally sutured.

Pre-Operative Use of Apparatus—Method A

FIG. 1: Proposed surgical margins drawn on skin.
FIG. 2: Apparatus sutured to skin, before surgery, in such a manner as to fold tumor upwards.
FIG. 3: Apparatus tightened and lateral areas are stretched.
FIG. 4: Side view of FIG. 3.
FIG. 7: Apparatus removed and tumor excised along proposed margins.
FIG. 8: Full thickness defect which results from excision of tumor. Edges have been prestretched.
FIG. 15: Relaxed defect is traditionally sutured.

Pre-Operative Use of Apparatus—Method B

FIG. 1: Proposed surgical margins drawn on skin.
FIG. 5: Apparatus sutured to skin, before surgery, in such a manner as to fold tumor beneath.
FIG. 6: Apparatus tightened and lateral areas are stretched.
FIGS. 7-8-15: As above.

Use of Apparatus as Post-Operative Retention Device

FIG. 16: Alternatively to FIG. 14, the active member can be substituted with a non-active member, and serve as a post-operative retention device after the wound has been traditionally sutured.

First Embodiment

Figure 17:
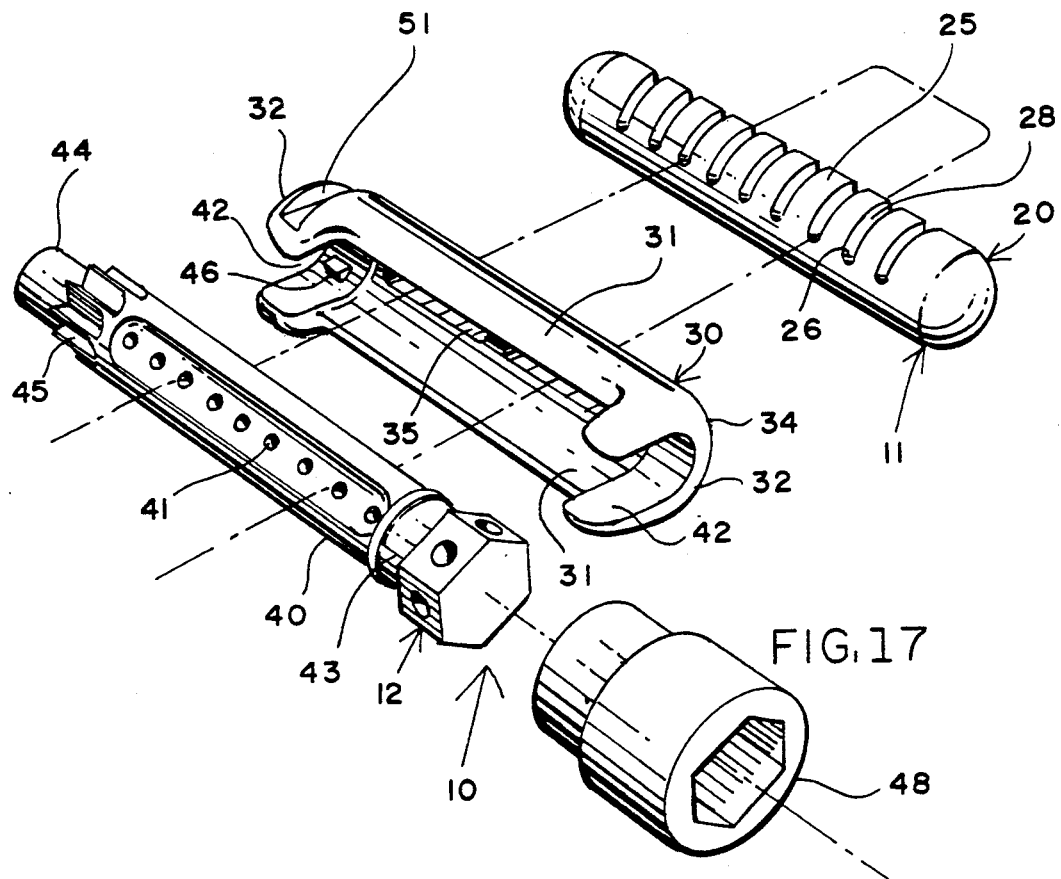
FIG. 17 is an exploded perspective view of a preferred first embodiment of the tension set showing the anchor at the upper right-hand portion with the winder and reel being respectively in the center and the lower left-hand portion.

The first embodiment of the subject tension set is shown in exploded perspective in FIG. 17, there it will be seen that the anchor 11 has a body 20, and its primary features are the suture guides 25 which have pockets 26 at the termination of the slot 28 defined between the guides 25.

The winder assembly of the first embodiment 12 has a body 30 with sides 31 and the underneath portion has a pair of linear slots 35 through which the suture 15 passes. The cradles 42 provided at the ends 32 include at one end the ratchet latch 46 and related stabilizer slot 51.

Finally at the left-hand portion of FIG. 16 the reel 40 will be seen which has a plurality of suture guides 41 aligned axially, and terminates in a pair of round members 44 which fit into the cradles 42 of the body portion 30. The end of the reel terminates with a crescent nut 49 which can accommodate retention wrench or a pin for rotating the same. Alternatively, a knurled knob 48 is provided to slip over the head 49 and additionally (not shown) a slip clutch may be inserted interiorly of the knurled knob 48 to prevent over tentioning of the sutures and the related portions of the skin being anchored by the sutures.

Figure 22:
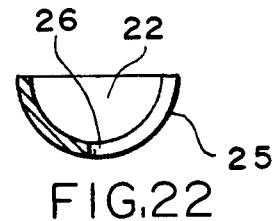
FIG. 22 is a transverse sectional view of the anchor body taken along section line 22—22 of FIG. 21.

Specific details of the first embodiment as just described in connection with FIG. 17 appear more specifically in FIGS. 19-26. There it will be seen at the upper portion that the anchor 11 includes the suture guides 25 which terminate at their lower end in suture pockets 26 and the guides 25 define suture slots 28 between them. The ends 22 are essentially rounded, and particularly as shown in FIG. 22, the slots 28 are crescent-shaped and approximate something slightly more than 90°.

Figure 23:
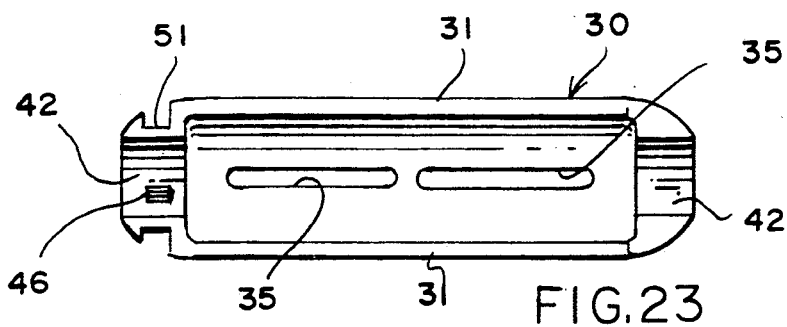
FIG. 23 is a plan view of the preferred winder body.
Figure 24:
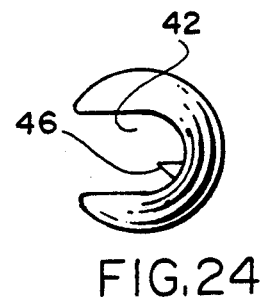
FIG. 24 is an end view of the preferred winder body.
Figure 25:
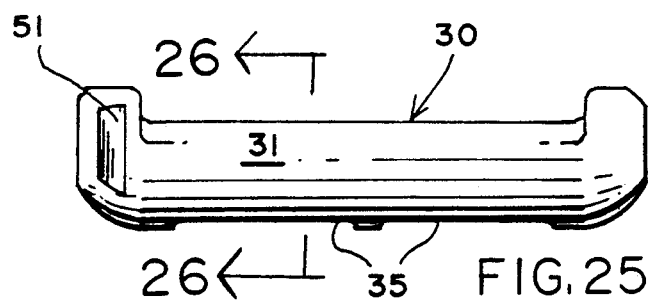
FIG. 25 is a side view of the preferred winder body.
Figure 26:
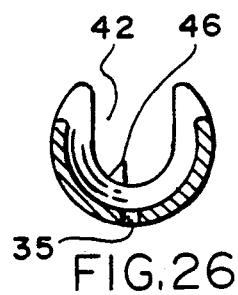
FIG. 26 is a transverse sectional view of the preferred winder body taken along section line 26—26 of FIG. 23.

In FIG. 23 it will be seen that the body 30 which houses the winder reel 40 includes the cradles 42 at each of the ends, and a pair of linearly aligned slots 35 which are adjacent the bottom 34 and that the suture guides 35 are approximately in a central portion of the bottom, particularly as shown in FIG. 26. The ratchet latch 46 is mounted in the cradle which includes the stabilizer slots 51 particularly as shown in FIG. 23.

Second Embodiment

Figure 18:
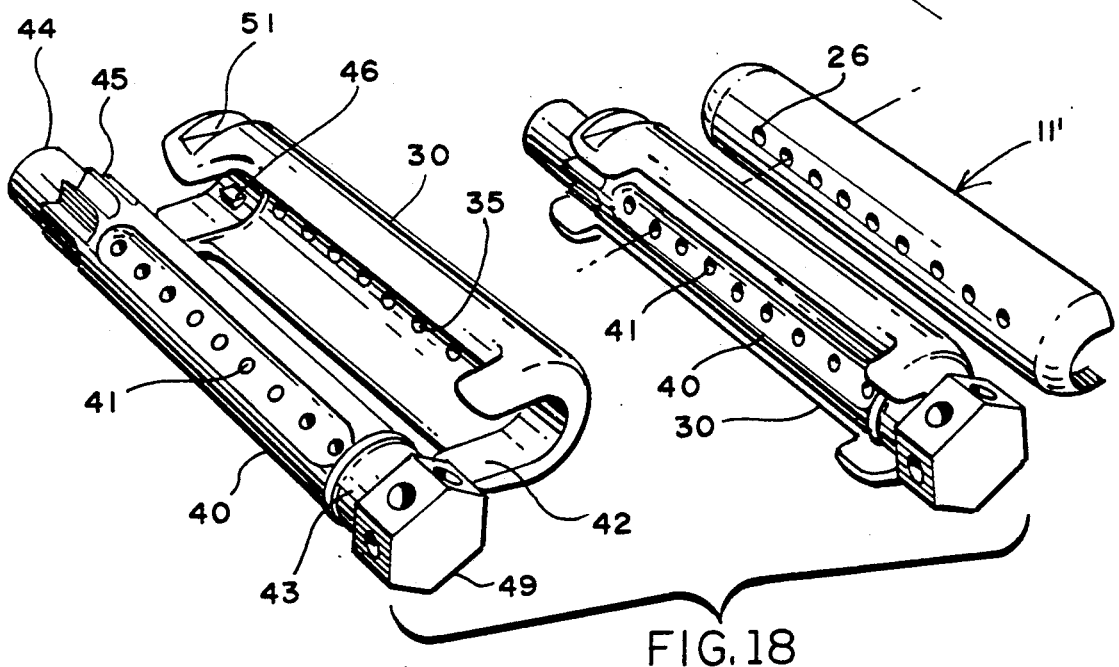
FIG. 18 is an alternative embodiment of that shown in FIG. 17 but with the members shown in nesting relationship as to the winder and exploded relationship as to the winder and reel.
Figure 19:
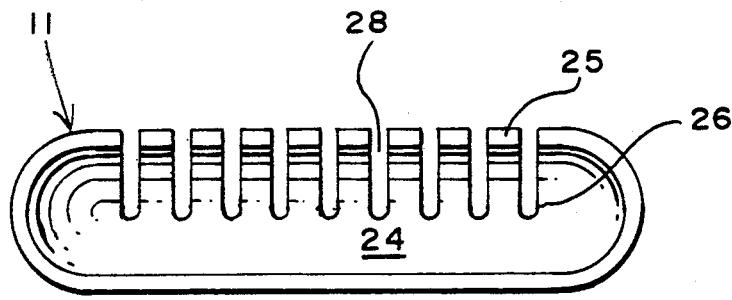
FIG. 19 is a plan view of the preferred anchor body.
Figure 20:
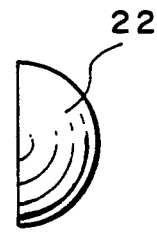
FIG. 20 is an end view of the preferred anchor body.
Figure 21:
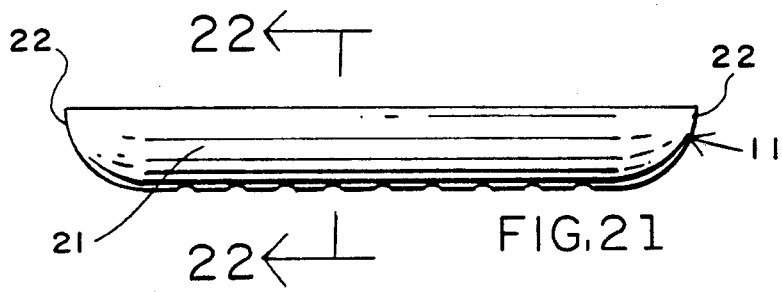
FIG. 21 is a side view of the preferred anchor body.

The second embodiment of the subject tension set 10 is shown in FIGS. 18 in exploded perspective. The same reference numerals will be used as in the description of the first embodiment since they are alternative modifications but which perform substantially the same function. Specifically the same reference numerals are used in FIG. 18 as FIG. 27 where the elements are substantially the same. The anchor of FIG. 27, however, is marked with an 11' for purposes of identifying the difference. The anchor of FIG. 18 is similarly identified with an 11'. As will be seen from right to left in FIG. 18, the anchor 11 has a plurality of pockets 26 for receiving the sutures. The second embodiment differs from the first embodiment primarily in that the pockets 26 in the second embodiment are holes in the bottom, whereas the pockets 26 in the first embodiment are the termination of slots 28 defined by the suture guides 25. The reel 40 of the second embodiment is substantially identical with that of the first embodiment. The same is true with regard to the winder body 30 with the exception that the winder body 30 has a plurality of holes 35 in its bottom which receive the sutures, rather than the linear slots 35 as with the first embodiment.

Figure 27:
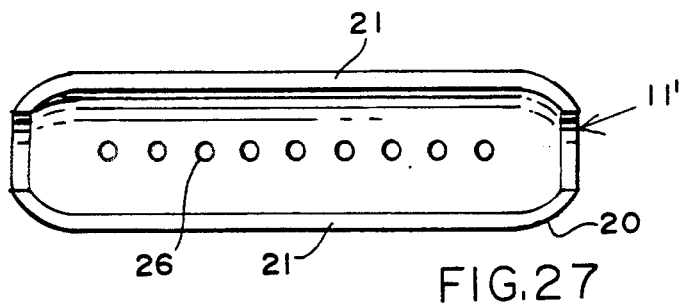
FIG. 27 is a plan view of an alternative embodiment anchor member.
Figure 28:
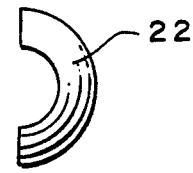
FIG. 28 is an end view of the alternative embodiment anchor member.
Figure 29:
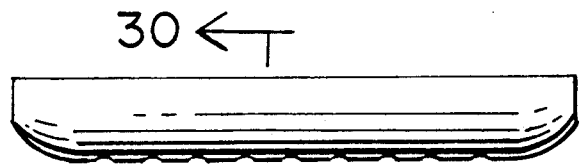
FIG. 29 is a front elevation side view of the alternative embodiment anchor member.
Figure 30:
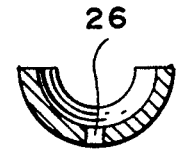
FIG. 30 is a transverse sectional view of the alternative embodiment anchor member taken along section line 30—30 of FIG. 29.
Figure 31:
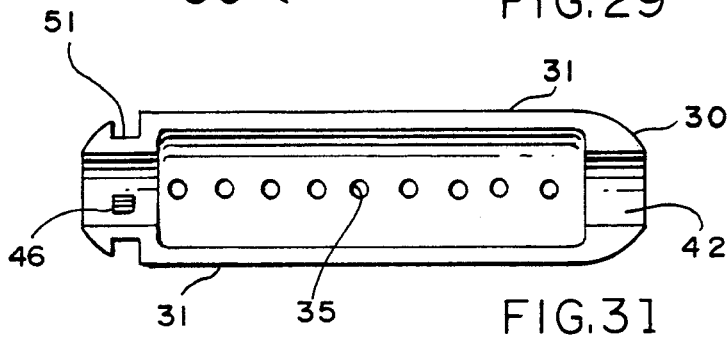
FIG. 31 is a plan view of the alternative embodiment body portion of the winder.
Figure 32:
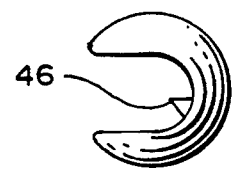
FIG. 32 is an end view of the alternative embodiment
Figure 33:
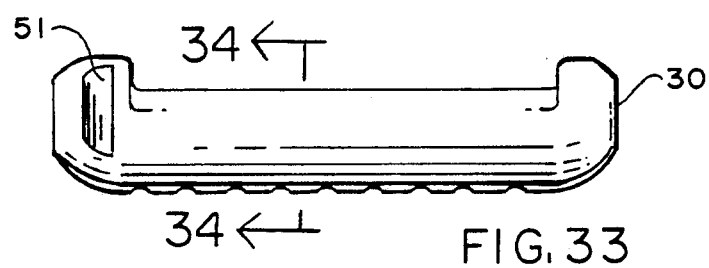
FIG. 33 is a front or side elevation of the alternative embodiment winder body.
Figure 34:
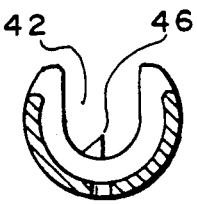
FIG. 34 is a transverse sectional view of the alternative embodiment winder body taken along section line 34—34 of FIG. 31.
Figure 35:
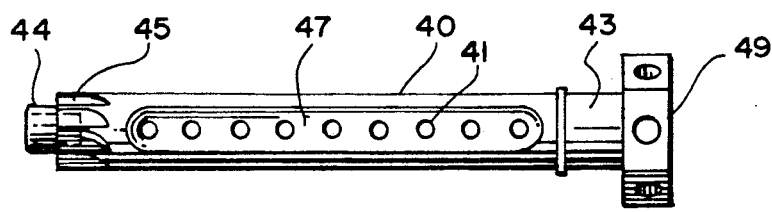
FIG. 35 is a plan view of the reel portion of the winder.
Figure 36:
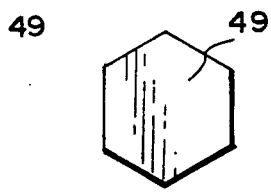
FIG. 36 is an end view of the reel portion of the winder.
Figure 37:
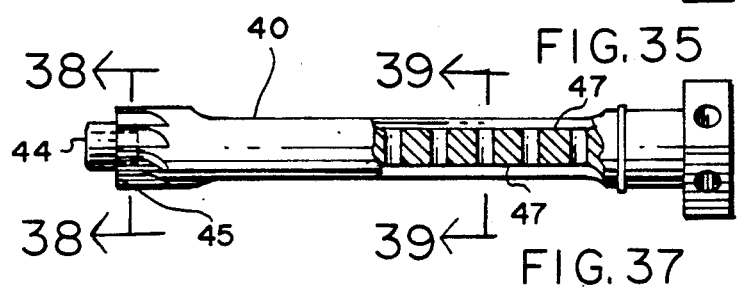
FIG. 37 is a partially broken sectional view along a side elevation of the reel of FIG. 35.

The specific details of the second embodiment appear primarily in FIGS. 27-34 where, beginning with FIG. 27, the anchor 11 is shown having a plurality of suture pockets 26 in the form of holes, the holes being formed in the bottom 24 between the sides 21.

The body 30 of the inner assembly 12 is shown in FIGS. 31-34 where it will be seen that a plurality of linearly spaced holes 41 are substituted for the slots 35 in the first embodiment. Otherwise, the second embodiment and the first embodiment are essentially the same.

Figures 38, 39:
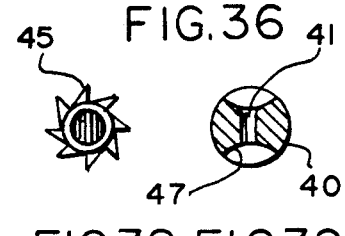
FIG. 38 is a transverse sectional view of the ratchet elements taken along section line 38—38 of FIG. 37.
FIG. 39 is a transverse sectional view of the suture guides of the alternative embodiment reel taken along section line 39—39 of FIG. 37.

Finally, FIGS. 35-39 show the reel 40 which is common to both embodiments. The body of the reel 40 has a plurality of linearly spaced suture guides 41 terminating with a ratchet 45 at one end, and a winder wheel 49 at the other. The general shape of the suture guides 41 is shown in FIG. 39 where it will be seen that flats 47 are cut into the opposed ends of the suture guides 41 with a tapered effect as shown in FIG. 39 to assist the surgeon in locating the suture guide 41 for insertion of the suture 15 and ultimate closure, knotting, and tensioning of the same.

In summary, numerous methods of closing the skin prior to or after a wound is prepared therein have been shown in connection with the description of FIGS. 1-16. Specifics of the first embodiment of the tension set 10 are shown in FIG. 17, and specifics of the second embodiment are shown in FIG. 18. The balance of the Figures relate to specific details of the elements which go into the tension set 10.

Although particular embodiments of the invention have been shown and described in full here, there is no intention to thereby limit the invention to the details of such embodiments. On the contrary, the intention is to cover all modifications, alternatives, embodiments, usages and equivalents as fall within the spirit and scope of the present invention, specification and appended claims.

What is claimed is:

1. The method of skin tensioning, stretching, or closing a wound using an interdependent anchor member and winder assembly member each adapted to be positioned in their respective entirety on opposite sides of the skin wound comprising the steps of:

preparing a wound on the skin that provides opposed skin margins, positioning a single anchor member at one side of the wound resting on the surface of the skin, positioning a single winder member containing a single reel at the opposite side of the wound resting on the surface of the skin, suturing through each respective member in its entirety and then through the skin beneath the respective member, on that respective member's side of the wound, using one continuous loop of suture material, providing the surgeon an unobstructed access to the space between the winder assembly and the anchor, while the skin engaged elements are drawn toward each other by rotation of the single reel in the winder assembly, and thereafter further winding the suture on the reel to eventually bring the margins of the wound into apposition for conventional suturing.

2. In the method of claim 1 above, providing a ratchet on the winder with spaced ratchet portions on the ratchet wheel, whereby the surgeon may predetermine by the number of ratchet passages the extent of the tension in the skin and the closure of the wound.

* * * * *